United States Patent
Giles et al.

(10) Patent No.: US 6,645,401 B2
(45) Date of Patent: Nov. 11, 2003

(54) CONJUGATED COPOLYMERS OF DITHIENOTHIOPHENE WITH VINYLENE OR ACETYLENE

(75) Inventors: Mark Giles, Southampton (GB); Louise Diane Farrand, Blandford Forum (GB); Martin Heeney, Southampton (GB); Maxim Shkunov, Southampton (GB); David Sparrowe, Bournemouth (GB); Steven Tierney, Southampton (GB); Marcus Thompson, Fordingbridge (GB); Iain McCulloch, Kings Somborne (GB)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/222,891

(22) Filed: Aug. 19, 2002

(65) Prior Publication Data
US 2003/0042471 A1 Mar. 6, 2003

(30) Foreign Application Priority Data
Aug. 17, 2001 (EP) .............................. 01118894

(51) Int. Cl.⁷ ........................ H01B 1/12; C09K 19/34; C07D 333/00
(52) U.S. Cl. ................. 252/500; 252/299.61; 528/377; 549/43; 427/384; 106/31.92
(58) Field of Search ............................ 252/500, 299.61; 528/377; 549/29, 43, 59; 427/384; 106/31.01, 31.92

(56) References Cited

U.S. PATENT DOCUMENTS

| 5,198,153 A | 3/1993 | Angelopoulos et al. |
| 5,892,244 A | 4/1999 | Tanaka et al. |
| 5,998,804 A | 12/1999 | Suh et al. |

FOREIGN PATENT DOCUMENTS

| EP | 0 528 662 | 2/1993 |
| EP | 0 889 350 | 1/1999 |
| WO | WO 96/21659 | 7/1996 |
| WO | WO 99/12989 | 3/1999 |
| WO | WO 00/79617 | 12/2000 |

OTHER PUBLICATIONS

Kossmehl et al "Poly(arylenealkenylene)s and poly(heteroarylenealkenylene)s . . . ", Makromolecular Chem, 183(11), 2771–86, 1982.*
Cervini et al "Synthesis of new conjugated thiophene polymers", Synthetic Metals, 76(1–3), 169–71 1996. Abstract Only.*
Kim et al (Nonlinear optical chromophores containing dithienothiophene as a new type of electron relay, J. Mater. Chem, 1999, 9, 2227–2232.*

* cited by examiner

Primary Examiner—Mark Kopec
(74) Attorney, Agent, or Firm—Millen, White, Zelano, Branigan, P.C.

(57) ABSTRACT

Conjugated copolymers of dithienothiophene with vinylene or acetylene are suitable for use as semiconductors or charge transport materials in optical, electrooptical or electronic devices including field effect transistors, electroluminescent, photovoltaic and sensor devices.

44 Claims, No Drawings

CONJUGATED COPOLYMERS OF DITHIENOTHIOPHENE WITH VINYLENE OR ACETYLENE

FIELD OF INVENTION

The invention relates to new conjugated copolymers of dithienothiophene with vinylene or acetylene (ethinylene). The invention further relates to methods of their preparation, to their use as semiconductors or charge transport materials in optical, electrooptical or electronic devices including field effect transistors, electroluminescent, photovoltaic and sensor devices. The invention further relates to field effect transistors and semiconducting components comprising the new polymers.

BACKGROUND AND PRIOR ART

Organic materials have recently shown promise as the active layer in organic based thin film transistors and organic field effect transistors [see reference 1]. Such devices have potential applications in smart cards, security tags and the switching element in flat panel displays. Organic materials are envisaged to have substantial cost advantages over their silicon analogues if they can be deposited from solution, as this enables a fast, large-area fabrication route.

The performance of the device is principally based upon the charge carrier mobility of the semiconducting material and the current on/off ratio, so the ideal semiconductor should have a low conductivity in the off state, combined with a high charge carrier mobility ($>1\times10^{-3}$ cm$^2$V$^{-1}$ s$^{-1}$). In addition, it is important that the semiconducting material is relatively stable to oxidation, i.e., it has a high ionisation potential, as oxidation leads to reduced device performance.

Compounds known in the prior art which have been shown to be effective p-type semiconductors for organic FETs are dithienothiophene (DTT) (1) and its fused dimer α,α'-bis(dithieno[3,2-b:2',3'-d]thiophene (BDT) (2) having the structures shown below [see reference 2–4].

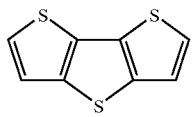

1 DTT

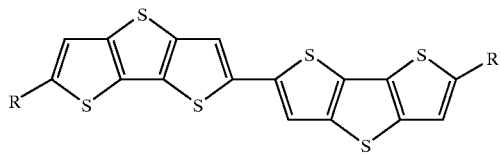

2 R = H BDT
3 R = Alkyl

In particular BDT, which has been extensively studied, has been shown to be an effective p-type semiconductor for organic FETs with a very high charge carrier mobility between $1\times10^{-3}$ and $5\times10^{-2}$ cm$^2$V$^{-1}$ s$^{-1}$ and very high current on/off ratios (up to $10^8$). BDT also has been found in the solid state to have a completely coplanar formation, and to be more planar than oligomers of thiophene.

However, BDT has a high melting point and is very insoluble, therefore, if used as the active layer in an organic thin film transistor, it cannot be readily solution processed. As a result, for applications like FETs, prior art materials like BDT are usually deposited as a thin film by vacuum deposition, which is an expensive processing technique that is unsuitable for the fabrication of large-area films. To improve the solubility of BDT, several substituted derivatives have so far been synthesized (3), [see reference 4] but these have still required vacuum processing when used in thin film transistors.

It is an aim of the present invention to provide new materials for use as semiconductors or charge transport materials, which are easy to synthesize, have high charge mobility and are easily processible to form thin and large-area films for use in semiconductor devices. Other aims of the invention are immediately evident to those skilled in the art from the following description.

The inventors have found that these aims can be achieved by providing new vinylene or acetylene copolymers of dithienothiophene (DTT).

Polymers containing DTT have been previously synthesised. DTT can be polymerised electrochemically but an insoluble material containing many structural defects is produced [see reference 5,6]. Similarly copolymers with dithienopyrrole have also been made (4) [see reference 7]. DTT has also been incorporated into vinylidene polymers either via Knoevenagel (5) [see reference 8] or Wittig reactions (6) [see reference 9]. The latter gave insoluble polymers, whereas the former produced polymers that were soluble but had only moderate photovoltaic or photoconductive behaviour.

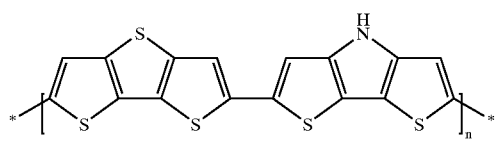

4

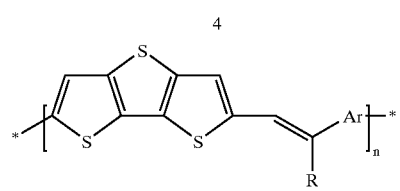

5 R = H, Ar = aryl
6 R = CN, Ar = aryl

DTT dimers and homo polymers of DTT and copolymers of DTT and thiophenes are reported in the international patent application WO 99/12989 [reference 10]. However, no characterisation or details of the synthetic route of the polymers are disclosed.

SUMMARY OF THE INVENTION

The invention relates to new conjugated copolymers comprising at least one dithienothiophene recurring unit and at least one vinylene or acetylene (ethinylene) recurring unit, wherein the dithienothiophene and the vinylene unit may be substituted or unsubstituted.

The invention further relates to the use of polymers according to the invention as semiconductors or charge transport materials, in particular in optical, electrooptical or electronic devices, like for example in field effect transistors (FET) as components of integrated circuitry, as thin film transistors in flat panel display applications or for Radio Frequency Identification (RFID) tags, or in semiconducting components for organic light emitting diode (OLED) applications such as electroluminescent displays or backlights of, e.g., liquid crystal displays, for photovoltaic or sensor devices, as electrode materials in batteries, as photoconductors and for electrophotographic applications like electrophotographic recording.

The invention further relates to a field effect transistor, for example as a component of integrated circuitry, as a thin film transistor in flat panel display applications, or in a Radio Frequency Identification (RFID) tag, comprising one or more poly(dithienothiophene vinylenes) according to the invention.

The invention further relates to a semiconducting component, for example in OLED applications like electroluminescent displays or backlights of, e.g., liquid crystal displays, in photovoltaic or sensor devices, as electrode materials in batteries, as photoconductors and for electrophotographic applications, comprising one or more poly (dithienothiophene vinylenes) according to the invention.

The invention further relates to a security marking or device comprising an RFID or ID tag or a FET according to the invention.

DETAILED DESCRIPTION OF THE INVENTION

Particularly preferred are oligo- and polymers having identical or different recurring units of formula I

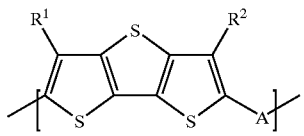

wherein
- $R^1$ and $R^2$ are independently of each other H, halogen or straight chain, branched or cyclic alkyl with 1 to 20 C-atoms, which may be unsubstituted, mono- or poly-substituted by F, Cl, Br, I or CN, it being also possible for one or more non-adjacent $CH_2$ groups to be replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl,
- $R^0$ and $R^{00}$ are independently of each other H or alkyl with 1 to 12 C-atoms,
- A is —$CX^1$=$CX^2$— or —C≡C—, and
- $X^1$ and $X^2$ are independently of each other H, F, Cl or CN.

Particularly preferred are oligo- and polymers of formulae I1 and I2

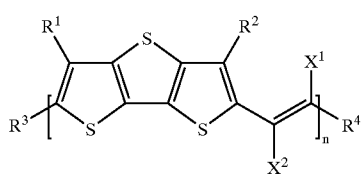

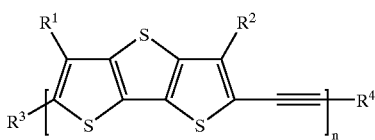

wherein $R^1$, $R^2$, $R^0$, $R^{00}$, $X^1$ and $X^2$ have independently of each other one of the meanings of formula I,
- $R^3$ and $R^4$ are independently of each other H, halogen, $Sn(R^0)_3$ or straight chain, branched or cyclic alkyl with 1 to 20 C-atoms, which may be unsubstituted, mono- or poly-substituted by F, Cl, Br, I, —CN and/or —OH, it being also possible for one or more non-adjacent $CH_2$ groups to be replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —CC— in such a manner that O and/or S atoms are not linked directly to one another, or optionally substituted aryl or heteroaryl,
- n is an integer from 1 to 10000, e.g., 2 to 10000, and wherein the recurring units may be identical or different.

Especially preferred are polymers of formula I, I1 and I2 having identical recurring units.

Further preferred are polymers of formula I, I1 and I2 wherein $R^1$ and $R^2$ are identical groups.

Especially preferred are polymers of formulae I, I1 and I2 having a degree of polymerisation (number of recurring units) from 2 to 5000, in particular from 10 to 5000, very preferably from 100 to 1000.

Further preferred are polymers of formulae I, I1 and I2 having a molecular weight from 5000 to 30000, in particular from 20000 to 100000

Further preferred are polymers of formulae I, I1 and I2 wherein $R^1$ and $R^2$ are selected from $C_1$-$C_{20}$-alkyl that is optionally substituted with one or more fluorine atoms, $C_1$-$C_{20}$-alkenyl, $C_1$-$C_{20}$-alkynyl, $C_1$-$C_{20}$-alkoxy, $C_1$-$C_{20}$-thioether, $C_1$-$C_{20}$-silyl, $C_1$-$C_{20}$-ester, $C_1$-$C_{20}$-amino, $C_1$-$C_{20}$-fluoroalkyl, $(CH_2CH_2O)_m$, with m being from 1 to 20, and optionally substituted aryl or heteroaryl.

Further preferred are polymers of formula I1 and I2 wherein $R^3$ and $R^4$ are selected from H, halogen, $Sn(R^0)_3$, $CH_2Cl$, COH, CH=$CH_2$, $SiR^0R^{00}$ and optionally substituted aryl or heteroaryl.

Aryl and heteroaryl preferably denote a mono-, bi- or tricyclic aromatic or heteroaromatic with up to 25 C atoms, wherein the rings can be fused, and in which the heteroaromatic groups contain at least one hetero ring atom, preferably selected from N, O and S. The aryl and heteroaryl groups are optionally substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —$NR^0$—, —$SiR^0R^{00}$—, —CO—, —COO—, —OCO—, —OCO—O, —S—CO—, —CO—S—, —CH=CH— or —C≡C— in such a manner that O and/or S atoms are not linked directly to one another.

Especially preferred aryl and heteroaryl groups are phenyl in which, in addition, one or more CH groups may be replaced by N, naphthalene, thiophene, thienothiophene, dithienothiophene, alkyl fluorene and oxazole, all of which can be unsubstituted, mono- or polysubstituted with L, wherein L is halogen or an alkyl, alkoxy, alkylcarbonyl or alkoxycarbonyl group with 1 to 12 C atoms, wherein one or more H atoms may be replaced by F or Cl.

If one of $R^1$ and $R^2$ is an alkyl or alkoxy radical, i.e., where the terminal $CH_2$ group is replaced by —O—, this may be straight-chain or branched. It is preferably straight-chain, has 2 to 8 carbon atoms and accordingly is preferably ethyl, propyl, butyl, pentyl, hexyl, heptyl, octyl, ethoxy, propoxy, butoxy, pentoxy, hexyloxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e., where one $CH_2$ group is replaced by —O—, is preferably straight-chain 2-oxapropyl (=methoxymethyl), 2- (=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8, or 9-oxadecyl, for example.

Fluoroalkyl is preferably $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$.

Halogen is preferably F or Cl.

The polymers according to the invention are especially useful as charge transport semiconductors in that they have high carrier mobilities. Particularly preferred are polymers wherein the DTT group is substituted by one or more alkyl or fluoroalkyl groups. The introduction of fluoroalkyl and alkyl side chains into the DTT group improves their solubility and therefore their solution processibility. Furthermore, the presence of fluoroalkyl side chains also renders them effective as n-type semiconductors. The electron-withdrawing nature of the fluoroalkyl substituents will also lower the HOMO (highest occupied molecular orbital) further and result in a more stable material, which is less susceptible to oxidation.

Furthermore, the polymers according to the present invention have good solution processibility. They are preferably prepared via soluble sulphonium precursor polymers (9) as depicted below in Scheme 1, in analogy to a route that was reported in the literature for polythiophenevinylene (PTV) [see reference 11, 12]. This route is particularly applicable to an all solution fabrication route in that after post heat treatment, the polymer will have significantly lower solubility and thus be inert to the subsequent solution processing route.

Scheme 1:

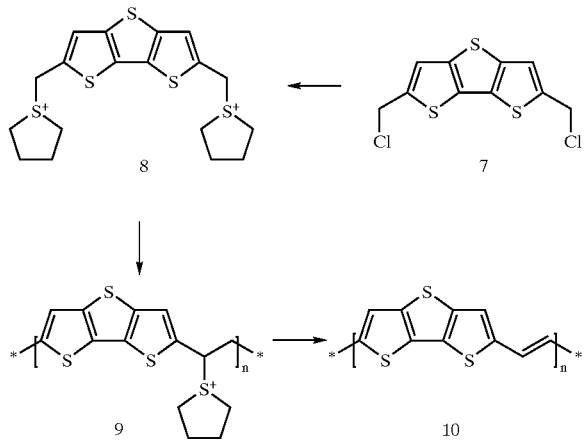

The sulphonium precursor polymer (9) has high solubility and good processibility, e.g. during the formation of thin film devices, and can be converted in situ, after film formation, into the fully conjugated conductive polymer (10) for example by heat treatment.

The sulphonium precursor polymers of the novel polymers are another aspect of the invention.

Especially preferred are precursor polymers having identical or different recurring units of formula Ia

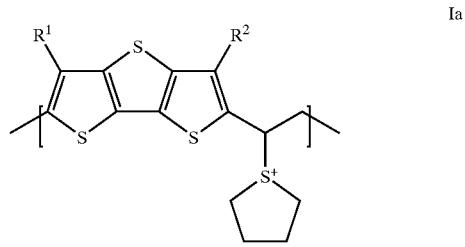

wherein $R^1$ and $R^2$ have independently of each other one of the meanings of formula I or the preferred meanings given above.

Especially preferred are precursor polymers of formula I1a

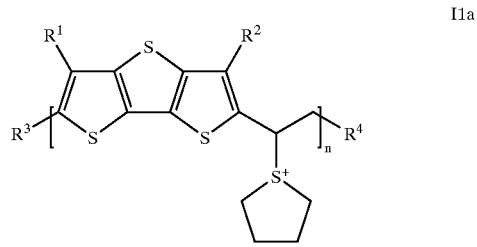

wherein $R^1$, $R^2$, $R^3$, $R^4$ and n are as defined in formula I1 and wherein the recurring units may be identical or different.

Another aspect of the invention relate to a method of forming a thin film, preferably with a thickness <1 micron, of a conjugated polymer according to the present invention, by applying a sulphonium precursor polymer of the conjugated polymer to a substrate, preferably from solution by known methods like for example spin-coating or common roll to roll processing techniques such as reverse gravure, followed by conversion of the precursor polymer into the conjugated polymer, for example by heat treatment The polymers of the present invention can be synthesized according to or in analogy to known methods. Some preferred methods are described below.

Synthesis of Unsubstituted Poly (dithienothiophene vinylenes) (PDTTVs) (Scheme 2)

The bischloromethyl-DTT (13) is reacted with butane-thiol and sodium hydroxide in the presence of a phase transfer catalyst in water to form the sulphide (24). The sulphide is oxidised to the sulphoxide (25) with hydrogen peroxide and TeO2 in methanol. Treatment of the monomer (25) with 1 equivalent of potassium tert-butoxide, followed by rapid quenching gives the sulphonium precursor polymer (26). This precursor polymer is soluble, for example during device formation can be deposited by spin coating onto the device. Heat treatment and elimination then leads to the required polymer (16). This route also has the advantage of giving an insoluble polymer that will not be effected by the coating of subsequent layers.

Scheme 2:

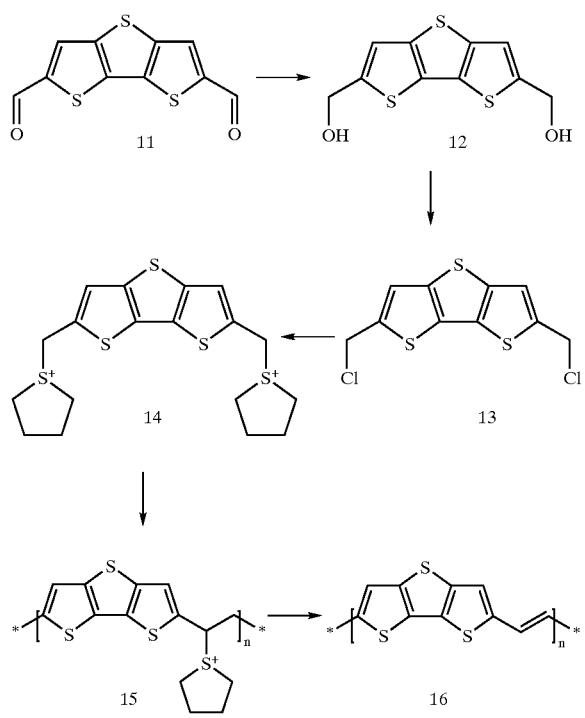

Synthesis of Unsubstituted PDTTVs (Scheme 3)

The bischloromethyl-DTT (13) is reacted with butanethiol and sodium hydroxide in the presence of a phase transfer catalyst in water to form the sulphide (24). The sulphide is oxidised to the sulphoxide (24) with hydrogen peroxide and $TeO_2$ in methanol. Treatment of the monomer (24) with 1 equivalent of potassium tert-butoxide, followed by rapid quenching gives the sulphonium precursor polymer (25). This precursor polymer is soluble, for example during device formation can be deposited by spin coating onto the device. Heat treatment and elimination then leads to the required polymer (16). This route also has the advantage of giving an insoluble polymer that will not be effected by the coating of subsequent layers.

Scheme 3:

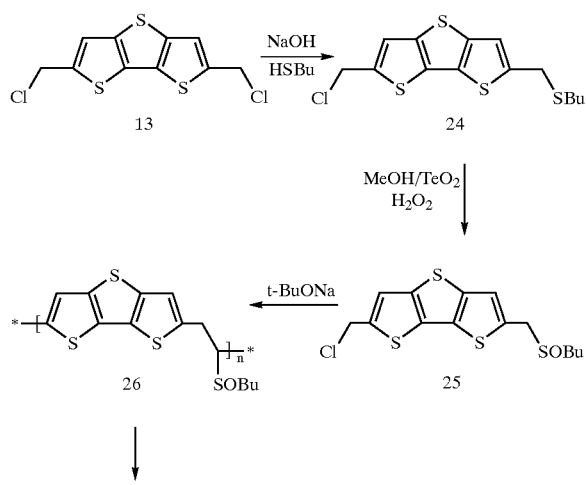

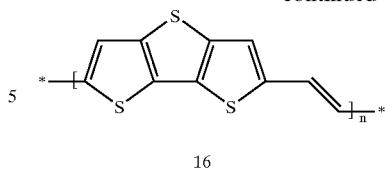

Synthesis of Substituted PDTTVs

Materials containing DDT that is substituted, for example with alkyl groups such as dihexyl DTT, have greater solubility than those containing unsubstituted DTT. This therefore increases the possible routes to vinylidene polymers [see reference 12].

McMurry Route (Scheme 4)

The Diformyl DTT derivative (17) can be reacted directly with titanium tetrachloride and zinc to yield directly the required polymer (19).

Gilch and Wessling Route (Scheme 4)

The Diformyl DTT derivative (17) can be reduced to the diol and then readily converted to the bischloromethyl-DTT (18). The bischloromethyl derivative can then be directly polymerised under Gilch conditions in the presence of potassium tert-butoxide to give a processable polymer (19). Alternatively reaction with tetrahydrothiophene yields the sulphonium monomer (20). Treatment of the monomer (20) with 1 equivalent of potassium tert-butoxide, followed by rapid quenching results in the sulphonium precursor (21). This is water-soluble and, for example during device formation can be deposited by spin coating onto the device. Heat treatment and elimination then leads to the required polymer (19). This route also has the advantage of giving an insoluble polymer that will not be affected by the coating of subsequent layers.

Scheme 4 (R', R'' = alkyl):

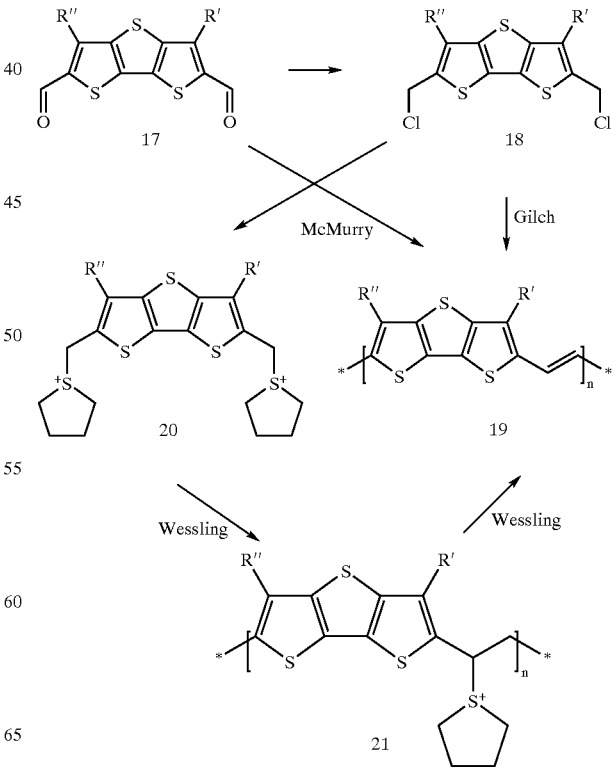

Stille Routes (Scheme 5)

The PDTTVs can also be made by cross coupling reaction. The dibromo DTT (22) can be coupled with bis(tributyl stannyl)ethene (23) under Stille conditions to yield the required polymer (19).

Scheme 5 (R', R'' = alkyl):

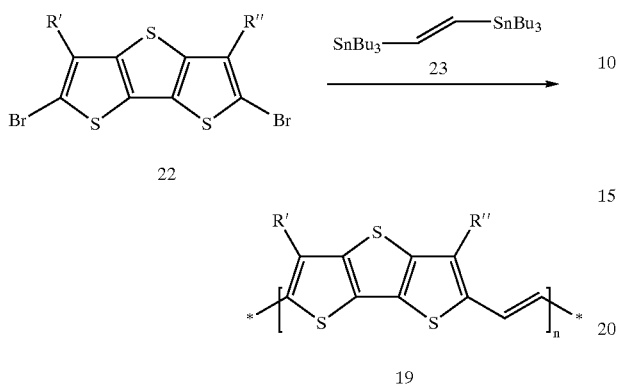

Alternative Precursor Route (Scheme 6)

The bischloromethyl-DTT (18) is reacted with butane-thiol and sodium hydroxide in the presence of a phase transfer catalyst in water to form the sulphide (27). The sulphide is oxidised to the sulphoxide (28) with hydrogen peroxide and TeO$_2$ in methanol. Treatment of the monomer (28) with 1 equivalent of potassium tert-butoxide, followed by rapid quenching gives the sulphonium precursor polymer (29). This precursor polymer is soluble, for example during device formation can be deposited by spin coating onto the device. Heat treatment and elimination then leads to the required polymer (19). This route also has the advantage of giving an insoluble polymer that will not be effected by the coating of subsequent layers.

Scheme 6 (R', R'' = alkyl):

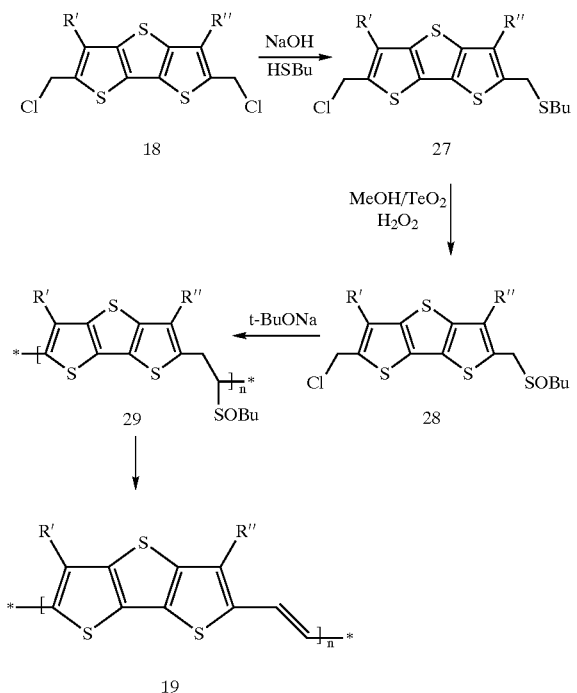

Synthesis of Poly(dithienothiophene ethinylenes) (Scheme 7)

DTT polymers containing the ethyne moiety can be made as shown below in scheme 7. Utilising the Stille methodology the dibromo DTT (22) can be coupled with bis(tributyl stannyl)ethyne (25) to yield the required polymer (41).

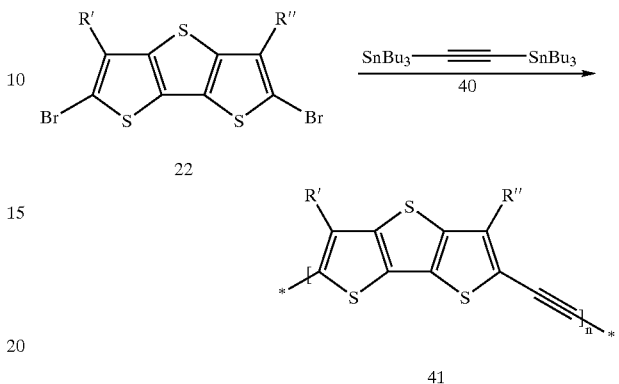

A further aspect of the invention relates to both the oxidised and reduced form of the polymers according to this invention. Either loss or gain of electrons results in formation of a highly delocalised ionic form, which is of high conductivity. This can occur on exposure to common dopants. Suitable dopants and methods of doping are known to those skilled in the art, e.g., from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, $La(NO_3)_3.6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds and materials of the present invention can be used as an organic "metal" in applications, for example, but not limited to, charge injection layers and ITO planarising layers in organic light emitting diode applications, films for flat panel displays and touch screens, antistatic films, printed conductive substrates, patterns or tracts in electronic applications such as printed circuit boards and condensers.

The polymers according to the present invention are useful as optical, electronic and semiconductor materials, in particular as charge transport materials in field effect transistors (FETs), e.g., as components of integrated circuitry, ID tags or TFT applications. Alternatively, they may be used in organic light emitting diodes (OLEDs) in electroluminescent display applications or as backlight of, e.g., liquid crystal displays, as photovoltaics or sensor materials, for electrophotographic recording, and for other semiconductor applications.

The polymers according to the invention show advantageous solubility properties which allow production processes using solutions of these compounds. Thus films, including layers and coatings, may be generated by low cost fabrication techniques, e.g., roll to roll solution coating. Suitable solvents or solvent mixtures comprise alkanes and/or aromatics, especially their fluorinated derivatives.

The polymers according to the present invention are useful as optical, electronic and semiconductor materials, in particular as charge transport materials in field effect transistors (FETs), as photovoltaics or sensor materials, for electrophotographic recording, and for other semiconductor applications. Such FETs, where an organic semiconductive material is arranged as a film between a gate-dielectric and a drain and a source electrode, are generally known e.g. from U.S. Pat. No. 5,892,244, WO 00/79617, U.S. Pat. No. 5,998,804, and from the references cited in the background and prior art chapter and listed below. Due to the advantages associated with this material, like low cost fabrication using the solubility properties of the materials according to the invention and thus the processibility of large surfaces, preferred applications of these FETs are such as integrated circuitry, TFT-displays and security applications.

In security applications, field effect transistors and other devices with semiconductive materials, like transistors or diodes, may be used for ID tags or security markings to authenticate and prevent counterfeiting of documents of value like banknotes, credit cards or ID cards, national ID documents, licenses or any product with money value, like stamps, tickets, shares, cheques, etc . . .

Alternatively, the polymers according to the invention may be used in organic light emitting devices or diodes (OLEDs), e.g., in display applications or as backlight of, e.g., liquid crystal displays. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive polymers may be employed in one or more of the charge transport layers and/or in the emission layer, corresponding to their electrical and/or optical properties. Furthermore their use within the emission layer is especially advantageous, if the polymers according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Meerholz, Synthetic Materials, 111–112, 2000, 31–34, Alcala, J. Appl. Phys., 88, 2000, 7124–7128 and the literature cited therein.

According to another use, the inventive polymers, especially those which show photoluminescent properties, may be employed as materials of light sources, e.g., of display devices such as described in EP 0 889 350 A1 or by C. Weder et al., Science, 279,1998, 835–837.

References
1. H. E. Katz, Z. Bao and S. L. Gilat, *Acc. Chem. Res.*, 2001, 34, 5, 359.
2. Sirringhaus, R. H. Friend, X. C. Li, S. C. Moratti, A. B. Holmes and N. Feeder, *Appl. Phys. Lett.*, 1997, 71, 26, 3871.
3. X. C. Li, H. Sirringhaus, F. Garnier, A. B. Holmes, S. C. Moratti, N. Feeder, W. Clegg, S. J. Teat and R. H. Friend, *J. Am. Chem. Soc.*, 1998, 120, 2206
4. J. J. Morrison, M. M. Murray, X. C. Li, A. B. Holmes, S. C. Moratti, R. H. Friend and H. Sirringhaus, *Synth. Met.*, 1999, 102, 987.
5. Arbizzani, C.; Catellani, M.; Mastragostino, M.; Cerroni, M. G. *Journal of Electroanalytical Chemistry* 1997, 423, 23–28.
6. Quattrochi, C.; Lazzaroni, R.; Brédas, J. I.; Zamboni, R.; C, T. *Macromolecules* 1993, 26, 1260–1264.
7. Campos, M.; Casalbore-Miceli, G.; Camaioni, N. *Journal of Physics D: Applied Physics* 1995, 28, 2123–2127.
8. Cervani, R.; Holmes, A. B.; Moratti, S. C.; Köhler, A.; Friend, R. H. *Synthetic Metals* 1996, 76, 169–171.
9. Koβmehl, G.; Belmling, P.; Manecke, G. *Makromolekulare Chemie* 1982, 183, 2771–2786.
10. WO 99/12989.
11. Fuchigami, H.; Tsumura, A.; H, K. *Applied Physics Letters* 1993, 63, 1372–1374.
12. Kraft, A.; Grimsdale, A. C.; Holmes, A. B. *Angewandte Chemie International version* 1998, 37, 402–428

The entire disclosure of all applications, patents and publications, cited above and below, and of corresponding European Patent application No. 01118894.3, filed Aug. 17, 2001 is hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A conjugated copolymer comprising at least one dithienothiophene recurring unit and at least one vinylene or acetylene (ethinylene) recurring unit, wherein the dithienothiophene is substituted by one or two $R^1$ groups and the vinylene group is unsubstituted or substituted by one or two $X^1$ groups, $R^1$ is halogen, optionally substituted aryl, optionally substituted heteroaryl, or straight chain, branched or cyclic alkyl with 1 to 20 C-atoms, which is unsubstituted, mono- or poly-substituted by F, Cl, Br, I or CN, and wherein one or more non-adjacent $CH_2$ groups can be replaced, in each case independently from one another, by —O—, —S—, —NH—, —NR°—, —SiR°R°°—, —CO—, —COO—, —CO—, —OCO—O—, —S—CO—, —CO—S—, —CH=CH— or —C≡C— in such a manner that O and/or S atoms are not linked directly to one another, and $X^1$ is F, Cl or CN.

2. A copolymer according to at least one of claim 1, having a degree of polymerisation from 10 to 5000.

3. A method of forming a thin film of a conjugated polymer according to claim 1, comprising:

applying a sulphonium precursor polymer of said conjugated polymer to a substrate from solution, and converting the precursor polymer into said conjugated polymer by heat treatment.

4. In optical, electrooptical or electronic devices, in components of integrated circuitry, in field effect transistors for example as thin film transistors in flat panel display applications or for RFID tags, and in semiconducting components for organic light emitting diode (OLED) applications, electroluminescent display devices, backlights, photovoltaic or sensor devices, and for electrophotographic applications, which contain semiconductors or charge transport materials, the improvement wherein one or more colpoymers according to claim 1 is used as a semiconductor or charge transport material.

5. In a field effect transistor (FET), OLED, electroluminescent device, RFID tag, backlight, photovoltaic or sensor device or electro-photographic recording device, the improvement wherein the device contains one or more copolymers according to claim 1.

6. In a security marking or device, the improvement wherein the marking or device contains one or more copolymers according to claim 1.

7. In a security marking or device, the improvement wherein the marking or device contains a FET or RFID tag according to claim 5.

8. A copolymer according to claim 1, wherein said copolymer is oxidatively or reductively doped.

9. In a charge injection layer, planarising layer, antistatic film or conducting substrate or pattern for electronic applications or flat panel displays, the improvement wherein a copolymer according to claim 8 is employed.

10. A copolymer according to claim 1, wherein
   $R^1$ is optionally substituted aryl, optionally substituted heteroaryl, 1 $C_1$–$C_{20}$-alkyl that is optionally substituted with one or more fluorine atoms, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester, $C_1$–$C_{20}$-amino, $C_1$–$C_{20}$-fluoroalkyl, or $(CH_2CH_2O)_m$, and
   m is 1 to 20.

11. A copolymer according to claim 10, wherein optionally substituted aryl is a mono-, bi- or tricyclic aromatic group with up to 25 C atoms, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —$NR^0$—, —$SiR^0R^{00}$—, —CO—, —COO—, —OCO—, —OCO—O, —S—CO—, —CO—S—, —CH=CH— or —CH≡C— in such a manner that O and/or S atoms are not linked directly to one another, and
   optionally substituted heteroaryl is a mono-, bi- or tricyclic heteroaromatic group with up to 25 C atoms containing groups contain at least one hetero ring atom selected from N, O and S, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —$NR^0$—, —$SiR^0R^{00}$—, —CO—, —COO—, OCO—, —OCO—O, —S—CO—, —CO—S—,—CH=CH— or —C≡C— in such a manner that O and/or S atoms are not linked directly to one another.

12. A copolymer according to claim 1, wherein $R^1$ is $C_1$–$C_{20}$-alkyl that is optionally substituted with one or more fluorine atoms, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester, $C_1$–$C_{20}$-amino, $C_1$–$C_{20}$-fluoroalkyl, $(CH_2CH_2O)_m$, with m being from 1 to 20, optionally substituted aryl, or optionally heteroaryl.

13. A copolymer according to claim 12, wherein optionally substituted aryl is a mono-, bi- or tricyclic aromatic group with up to 25 C atoms, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —$NR^0$—, —$SiR^0R^{00}$—, —CO—, —COO—, OCO—, —OCO—O, —S—CO—, —CO—S—,—CH=CH— or —C≡C— in such a manner that O and/or S atoms are not linked directly to one another, and
   optionally substituted heteroaryl is a mono-, bi- or tricyclic heteroaromatic group with up to 25 C atoms containing groups contain at least one hetero ring atom selected from N, O and S, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —$NR^0$—, —$SiR^0R^{00}$—, —CO—, —COO—, OCO—, —OCO—O, —S—CO—, —CO—S—,—CH=CH— or —C≡C— in such a manner that O and/or S atoms are not linked directly to one another.

14. A copolymer according to claim 1, wherein optionally substituted aryl is a mono-, bi- or tricyclic aromatic group with up to 25 C atoms, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —$NR^0$—, —$SiR^0R^{00}$—, —CO—, —COO—, OCO—, —OCO—O, —S—CO—, —CO—S—,—CH=CH— or —C≡C— in such a manner that O and/or S atoms are not linked directly to one another, and
   optionally substituted heteroaryl is a mono-, bi- or tricyclic heteroaromatic group with up to 25 C atoms containing groups contain at least one hetero ring atom selected from N, O and S, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —$NR^0$—, —$SiR^0R^{00}$—, —CO—, —COO—, OCO—, —OCO—O, —S—CO—, —CO—S—, —CH=CH— or —C≡C— in such a manner that O and/or S atoms are not directly to one another.

15. A conjugated copolymer comprising at least one dithienothiophene recurring unit and at least one vinylene or acetylene (ethinylene) recurring unit,
   wherein the dithienothiophene is unsubstituted or substituted by one or two $R^1$ groups and the vinylene group is substituted by one or two $X^1$ groups, R¹ is halogen, optionally substituted aryl, optionally substituted heteroaryl, or straight chain, branched or cyclic alkyl with 1 to 20 C-atoms, which is unsubstituted, mono- or poly-substituted by F, Cl, Br, I or CN, and wherein one or more non-adjacent CH₂ groups can be replaced, in each case independently from one another, by —O—, —S—, —NH—, —NR°—, —SiR°R°°—, —CO—, —COO—, —OCO—, —OCO—O—, —S—CO—, —CO—S—, —CH=CH— or —C≡C— in such a manner that O and/or S atoms are not linked directly to one another, and X¹ is F or Cl.

16. A polymer having identical or different recurring units selected of formula Ia

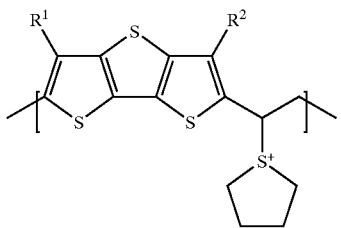

wherein

R¹ and R² are independently of each other H, halogen, optionally substituted aryl, optionally substituted heteroaryl, or straight chain, branched or cyclic alkyl with 1 to 20 C-atoms, which is unsubstituted, mono- or poly-substituted by F, Cl, Br, I or CN, and wherein one or more non-adjacent CH₂ groups can be replaced, in each case independently from one another, by —O—, —S—, —NH—, —NR°—, —SiR°R°°—, —CO—, —COO—, —OCO—, —OCO—O—, —S—CO—, —CO—S—, —CH=CH— or —C≡C— in such a manner that O and/or S atoms are not linked directly to one another.

17. A polymer of claim 16, wherein said polymer is of formula I1a

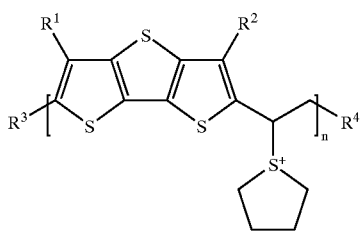

wherein

R³ and R⁴ are independently of each other H, halogen, optionally substituted aryl, optionally substituted heteroaryl, Sn(R°)₃, or straight chain, branched or cyclic alkyl with 1 to 20 C-atoms, which is unsubstituted, mono- or poly-substituted by F, Cl, Br, I, —CN and/or —OH, and wherein one or more non-adjacent CH₂ groups can be replaced, in each case independently from one another, by —O—, —S—, —NH—, —NR0—, —SiR°R°°—, —CO—, —COO—, —OCO—, —OCO—O—, —S—CO—, —CO—S—, —CH=CH— or —CC— in such a manner that O and/or S atoms are not linked directly to one another, and wherein the recurring units may be identical or different.

18. A copolymer according to clam 17, wherein optionally substituted aryl is a mono-, bi- or tricyclic aromatic group with up to 25 C atoms, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent CH₂ groups are optionally replaced, in each case independently from one another, by —O—, —S—, —NH—, —NR°—, —SiR°R°°—, —CO—, —COO—, OCO—, —OCO—O, —S—CO—, —CO—S—,—CH=CH— or —C≡C— in such a manner that O and/or S atoms are not linked directly to one another, and optionally substituted heteroaryl is a mono-, bi- or tricyclic heteroaromatic group with up to 25 C atoms containing groups contain at least one hetero ring atom selected from N, O and S, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent CH₂ groups are optionally replaced, in each case independently from one another, by —O—, —S—, —NH—, —NR°—, —SiR°R°°—, —CO—, —COO—, OCO—, —OCO—O, —S—CO—, —CO—S—,—CH=CH— or —C≡C— in such a manner that O and/or S atoms are not linked directly to one another.

19. A copolymer according to claim 16, wherein optionally substituted aryl is a mono-, bi- or tricyclic aromatic group with up to 25 C atoms, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent CH₂ groups are optionally replaced, in each case independently from one another, by —O—, —S—, —NH—, —NR°—, —SiR°R°°—, —CO—, —COO—, OCO—, —OCO—), —S—, —CO—S—,—CH=CH— or —C≡C— in such a manner that O and/or S atoms are not linked directly to one another, and optionally substituted heteroaryl is a mono-, bi- or tricyclic heteroaromatic group with up to 25 C atoms containing groups contain at least one hetero ring atom selected from N, O and S, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent CH₂ groups are optionally replaced, in each case independently from one another, by —O—, —S—, —NH—, —NR°—, —SiR°R°°—, —CO—, —COO—, OCO—, —OCO—O, —S—CO—, —CO—S—,—CH=CH— or —C≡C— in such a manner that O and/or S atoms are not linked directly to one another.

20. A conjugated copolymer comprising at least one dithienothiophene recurring unit and at least one vinylene or acetylene (ethinylene) recurring unit, wherein said copolymer has identical or different recurring units selected of formula I

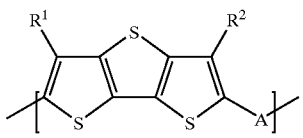

I wherein
R$^1$ and R$^2$ are independently of each other H, halogen, optionally substituted aryl, optionally substituted heteroaryl, or straight chain, branched or cyclic alkyl with 1 to 20 C-atoms, which is unsubstituted, mono- or poly-substituted by F, Cl, Br, I or CN, and wherein one or more non-adjacent CH$_2$ groups can be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, R$^0$ and R$^{00}$ are independently of each other H or alkyl with 1 to 12 C-atoms, A is —CX$^1$=CX$^2$— or —C≡C—, and X$^1$ and X$^2$ are independently of each other H, F. Cl or CN.

21. A copolymer according to claim 20, wherein said coplymer is of formula I1 and I2

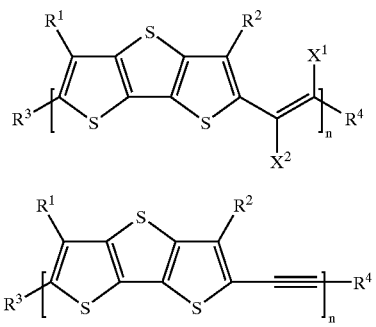

wherein
R$^3$ and R$^4$ are independently of each other H, halogen, optionally substituted aryl, optionally substituted heteroaryl, Sn(R$^0$)$_3$, or straight chain, branched or cyclic alkyl with 1 to 20 C-atoms, which is unsubstituted, mono- or poly-substituted by F, Cl, Br, I, —CN and/or —OH, and wherein one or more non-adjacent CH$_2$ groups can be replaced, in each case independently from one another, by —O—, —S—, —NH—, —NR0—, —SiR$^0$R$^{00}$—, —CO—, —COO—, —OCO—, —OCO—O—, —S—CO—, —CO—S—, —CH=CH— or —CC— in such a manner that O and/or S atoms are not linked directly to one another, and n is an integer from 1 to 10000,
wherein the recurring units may be identical or different.

22. A copolymer according to claim 21, wherein
R$^1$ and R$^2$ are selected from optionally substituted aryl, optionally substituted heteroaryl, C$_1$–C$_{20}$-alkyl that is optionally substituted with one or more fluorine atoms, C$_1$–C$_{20}$-alkenyl, C$_1$–C$_{20}$-alkynyl, C$_1$–C$_{20}$-alkoxy, C$_1$–C$_{20}$-thioether, C$_1$–C$_{20}$-silyl, C$_1$–C$_{20}$-ester, C$_1$–C$_{20}$-amino, C$_1$–C$_{20}$-fluoroalkyl, or (CH$_2$CH$_2$O)$_m$, and
m is 1 to 20.

23. A copolymer according to claim 22, wherein optionally substituted aryl is a mono-, bi- or tricyclic aromatic group with up to 25 C atoms, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent CH$_2$ groups are optionally replaced, in each case independently from one another, by —O—, —S—, —NH—, —NR$^0$—, —SiR$^0$R$^{00}$—, —CO—, —COO—, OCO—, —OCO—O, —S—CO—, —CO—S—,—CH=CH— or —C≡C— in such a manner that O and/or S atoms are not linked directly to one another, and optionally substituted heteroaryl is a mono-, bi- or tricyclic heteroaromatic group with up to 25 C atoms containing groups contain at least one hetero ring atom selected from N, O and S, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent CH$_2$ groups are optionally replaced, in each case independently from one another, by —O—, —S—, —NH—, —NR$^0$—, —SiR$^0$R$^{00}$—, —CO—, —COO—, OCO—, —OCO—O, —S—CO—, —CO—S—,—CH=CH— or —C≡C— in such a manner that O and/or S atoms are not linked directly to one another.

24. A copolymer according to claim 22, wherein R$^3$ and R$^4$ are selected from H, halogen, Sn(R$^0$)$_3$, CH$_2$Cl, COH, CH=CH$_2$,SiR$^0$R$^{00}$, optionally substituted aryl, and optionally substituted heteroaryl.

25. A copolymer according to claim 24, wherein optionally substituted aryl is a mono-, bi- or tricyclic aromatic group with up to 25 C atoms, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent CH$_2$ groups are optionally replaced, in each case independently from one another, by —O—, —S—, —NH—, —NR$^0$—, —SiR$^0$R$^{00}$—, —CO—, —COO—, OCO—, —OCO—O, —S—CO—, —CO—S—,—CH=CH— or —C≡C— in such a manner that O and/or S atoms are not linked directly to one another, and optionally substituted heteroaryl is a mono-, bi- or tricyclic heteroaromatic group with up to 25 C atoms containing groups contain at least one hetero ring atom selected from N, O and S, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent CH$_2$ groups are optionally replaced, in each case independently from one another, by —O—, —S—, —NH—, —NR$^0$—, —SiR$^0$R$^{00}$—, —CO—, —COO—, OCO—, —OCO—O, —S—CO—, —CO—S—,—CH=CH— or —C≡C— in such a manner that O and/or S atoms are not directly to one another.

26. A copolymer according to claim 21, wherein R$^3$ and R$^4$ are selected from H, halogen, Sn(R$^0$)$_3$, CH$_2$Cl, COH, CH=CH$_2$, SiR$^0$R$^{00}$, optionally substituted aryl, and optionally substituted heteroaryl.

27. A copolymer according to at least one of claim 26, having a degree of polymerisation from 10 to 5000.

28. A copolymer according to claim 26, wherein optionally substituted aryl is a mono-, bi- or tricyclic aromatic group with up to 25 C atoms, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —$NR^0$—, —$SiR^0R^{00}$—, —CO—, —COO—, OCO—, —OCO—O, —S—CO—, —CO—S—, —CH=CH— or —C≡C— in such a manner that O and/or S atoms are not linked directly to one another, and optionally substituted heteroaryl is a mono-, bi- or tricyclic heteroaromatic group with up to 25 C atoms containing groups contain at least one hetero ring atom selected from N, O and S, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —$NR^0$—, —$SiR^0R^{00}$—, —CO—, —COO—, OCO—, —OCO—O, —S—CO—, —CO—S—, —CH=CH— or —C≡C— in such a manner that O and/or S atoms are not directly to one another.

29. A copolymer according to at least one of clam 21, having a degree of polymerisation from 10 to 5000.

30. A copolymer according to claim 21, wherein optionally substituted aryl is a mono-, bi- or tricyclic aromatic group with up to 25 C atoms, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —$NR^0$—, —$SiR^0R^{00}$—, —CO—, —COO—, OCO—, —OCO—O, —S—CO—, —CO—S—, —CH=CH— or —C≡C— in such a manner that O and/or S atoms are not linked directly to one another, and optionally substituted heteroaryl is a mono-, bi- or tricyclic heteroaromatic group with up to 25 C atoms containing groups contain at least one hetero ring atom selected from N, O and S, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —$NR^0$—, —$SiR^0R^{00}$—, —CO—, —COO—, OCO—, —OCO—O, —S—CO—, —CO—S—, —CH=CH— or —C≡C— in such a manner that O and/or S atoms are not directly to one another.

31. A copolymer according to claim 20, wherein $R^1$ and $R^2$ are selected from optionally substituted aryl, optionally substituted heteroaryl, $C_1$–$C_{20}$-alkyl that is optionally substituted with one or more fluorine atoms, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester, $C_1$–$C_{20}$-amino, $C_1$–$C_{20}$-fluoroalkyl, or $(CH_2CH_2O)_m$, and m is 1 to 20.

32. A copolymer according to claim 31, wherein $R^3$ and $R^4$ are selected from H, halogen, $Sn(R^0)_3$, $CH_2Cl$, COH, $CH=CH_2$, $SiR^0R^{00}$, optionally substituted aryl, and optionally substituted heteroaryl.

33. A copolymer according to claim 32, wherein optionally substituted aryl is a mono-, bi- or tricyclic aromatic group with up to 25 C atoms, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —$NR^0$—, —$SiR^0R^{00}$—, —CO—, —COO—, OCO—, —OCO—O, —S—CO—, —CO—S—, —CH=CH— or —C≡C— in such a manner that O and/or S atoms are not linked directly to one another, and optionally substituted heteroaryl is a mono-, bi- or tricyclic heteroaromatic group with up to 25 C atoms containing groups contain at least one hetero ring atom selected from N, O and S, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —$NR^0$—, —$SiR^0R^{00}$—, —CO—, —COO—, OCO—, —OCO—O, —S—CO—, —CO—S—, —CH=CH— or —C≡C— in such a manner that O and/or S atoms are not directly to one another.

34. A copolymer according to at least one of claim 31, having a degree of polymerisation from 10 to 5000.

35. A copolymer according to claim 31, wherein optionally substituted aryl is a mono-, bi- or tricyclic aromatic group with up to 25 C atoms, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —$NR^0$—, —$SiR^0R^{00}$—, —CO—, —COO—, OCO—, —OCO—O, —S—CO—, —CO—S—, —CH=CH— or —C≡C— in such a manner that O and/or S atoms are not linked directly to one another, and optionally substituted heteroaryl is a mono-, bi- or tricyclic heteroaromatic group with up to 25 C atoms containing groups contain at least one hetero ring atom selected from N, O and S, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —$NR^0$—, —$SiR^0R^{00}$—, —CO—, —COO—, OCO—, —OCO—O, —S—CO—, —CO—S—, —CH=CH— or —C≡C— in such a manner that O and/or S atoms are not directly to one another.

36. A copolymer according to at least one of claim 20, having a degree of polymerisation from 10 to 5000.

37. A method of forming a thin film of a conjugated polymer according to claim 20, comprising:

applying a sulphonium precursor polymer of said conjugated polymer to a substrate from solution, and converting the precursor polymer into said conjugated polymer by heat treatment.

38. In optical, electrooptical or electronic devices, in components of integrated circuitry, in field effect transistors for example as thin film transistors in flat panel display applications or for RFID tags, and in semiconducting components for organic light emitting diode (OLED) applications, electroluminescent display devices, backlights, photovoltaic or sensor devices, and for electrophotographic applications, which contain semiconductors or charge transport materials, the improvement wherein one or more colpoymers according to claim 20 is used as a semiconductor or charge transport material.

39. A copolymer according to claim 20, wherein said coplymer is oxidatively or reductively doped.

40. In a charge injection layer, planarising layer, antistatic film or conducting substrate or pattern for electronic applications or flat panel displays, the improvement wherein a copolymer according to claim 39 is employed.

41. A copolymer according to claim 20, wherein optionally substituted aryl is a mono-, bi- or tricyclic aromatic group with up to 25 C atoms, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent CH$_2$ groups are optionally replaced, in each case independently from one another, by —O—, —S—, —NH—, —NR$^0$—, —SiR$^0$R$^{00}$—, —CO—, —COO—, OCO—, —OCO—O, —S—CO—, —CO—S—, —CH=CH— or —C≡C— in such a manner that O and/or S atoms are not linked directly to one another, and optionally substituted heteroaryl is a mono-, bi- or tricyclic heteroaromatic group with up to 25 C atoms containing groups contain at least one hetero ring atom selected from N, O and S, wherein the rings can be fused, and which is unsubstituted or substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent CH$_2$ groups are optionally replaced, in each case independently from one another, by —O—, —S—, —NH—, —NR$^0$—, —SiR$^0$R$^{00}$—, —CO—, —COO—, OCO—, —OCO—O, —S—CO—, —CO—S—,—CH=CH— or —C≡C— in such a manner that O and/or S atoms are not directly to one another.

42. In a field effect transistor (FET), OLED, electroluminescent device, RFID tag, backlight, photovoltaic or sensor device or electro-photographic recording device, the improvement wherein the device contains one or more copolymers according to claim 20.

43. In a security marking or device, the improvement wherein the marking or device contains one or more copolymers according to claim 20.

44. In a security marking or device, the improvement wherein the marking or device contains a FET or RFID tag according to claim 43.

* * * * *

UNITED STATES PATENT AND TRADEMARK OFFICE
CERTIFICATE OF CORRECTION

PATENT NO. : 6,645,401 B2
DATED : November 11, 2003
INVENTOR(S) : Mark Giles et al.

It is certified that error appears in the above-identified patent and that said Letters Patent is hereby corrected as shown below:

Column 12,
Line 52, "—COO—, —CO—," should read -- —COO—, —OCO—, --.
Line 57, "at least one of claim 1" should read -- claim 1 --.

Column 13,
Line 7, "colpoymers" should read -- copolymers --.
Line 29, "heteroaryl, 1 $C_1$—$C_{20}$-alkyl" should read -- heteroaryl, $C_1$—$C_{20}$-alkyl --.
Line 45, "—OCO—O," should read -- —OCO—O—, --.
Line 50, "containing groups contain at least one" should read -- containing at least one --.
Line 60, "OCO—, —OCO—O," should read -- —OCO—,—OCO—O—, --.

Column 14,
Line 14, "OCO—, —OCO—O," should read -- —OCO—, —OCO—O—, --.
Line 19, "containing groups contain at least one" should read -- containing at least one --.
Line 29, "OCO—, —OCO—O," should read ---OCO—, —OCO—O—, --
Line 43, "OCO—, —OCO—O," should read -- —OCO—, —OCO—O—, --.
Line 48, "containing groups contain at least one" should read — containing at least one --.
Line 58, "OCO—, —OCO—O," should read -- —OCO—, —OCO—O—, --
Line 60, "are not directly" should read -- are not linked directly --.

Column 15,
Line 62, "—NR0—," should read -- —NR$^0$ --.

Column 16,
Line 1, "clam 17," should read -- claim 17, --.
Line 11, "OCO—, —OCO—O," should read -- —OCO—, —OCO—O—, --
Line 16, "containing groups contain at least one" should read -- containing at least one --.
Line 28, "OCO—, —OCO—O," should read -- —OCO—, —OCO—O—,
Line 43, "OCO—, —OCO—), —S—," should read -- —OCO—, —OCO—O—, —S—CO—, --
Line 48, "containing groups contain at least one" should read -- containing at least one --.
Line 58, "OCO—, —OCO—O," should read -- —OCO—, —OCO—O—, Column 17,
Line 25, "H, F. Cl" should read -- H, F, Cl --.
Line 27, "coplymer" should read -- copolymer --.
Line 52, "—NR0—" should read -- —NR$^0$ --.

UNITED STATES PATENT AND TRADEMARK OFFICE
CERTIFICATE OF CORRECTION

PATENT NO.    : 6,645,401 B2
DATED         : November 11, 2003
INVENTOR(S)   : Mark Giles et al.

It is certified that error appears in the above-identified patent and that said Letters Patent is hereby corrected as shown below:

Column 18,
Line 11, "OCO—, —OCO—O," should read -- —OCO—, —OCO—O—, --.
Line 16, "containing groups contain at least one" should read -- containing at least one --.
Line 26, "OCO—, —OCO—O," should read -- —OCO—, —OCO—O—, --.
Line 31, "CH=CH$_2$,SiR°R00 " should read -- CH=CH$_2$, SiR$^0$R$^{00}$, --.
Line 43, "OCO—, —OCO—0," should read —OCO—, —OCO—O—, --.
Line 48, "containing groups contain at least one" should read -- containing at least one --.
Line 58, "OCO—, —OCO—O," should read -- —OCO—, —OCO—O—, --.
Line 60, "are not directly" should read -- are not linked directly --.
Line 66, "at least one of claim 26" should read -- claim 26 --.

Column 19,
Line 11, "OCO—, —OCO—O," should read --OCO—, —OCO—O—, --.
Line 16, "containing groups contain at least one" should read -- containing at least one --.
Line 26, "OCO—, —OCO—O," should read -- —OCO—, —OCO—O—, --.
Line 28, "are not directly" should read -- are not linked directly --.
Line 30, "at least one of clam 21" should read -- claim 21 --.
Line 41, "OCO—, —OCO—O," should read -- —OCO—, —OCO—O—, --.
Line 46, "containing groups contain at least one" should read -- containing at least one --.
Line 56, "OCO—, —OCO—O," should read -- —OCO—, —OCO—O—, --.
Line 58, "are not directly" should read -- are not linked directly –.

Column 20,
Line 15, "OCO—, —OCO—O," should read -- —OCO—, —OCO—O—, --.
Line 20, "containing groups contain at least one" should read -- containing at least one --.
Line 31, "OCO—, —OCO—O" should read -- —OCO—, —OCO—O—, --.
Line 33, "are not directly" should read -- are not linked directly --.
Line 35, "at least one of claim 31" should read -- claim 31 --.
Line 47, "OCO—, —OCO—O," should read -- -OCO—, —OCO—O—, --.
Line 52, "containing groups contain at least one" should read – containing at least one --.
Line 62, "OCO—, —OCO—O," should read ---OCO—, —OCO—O—, --.
Line 64, "are not directly" should read – are not linked directly --.
Line 66, "at least one of claim 20" should read -- claim 20 --.

Column 21,
Line 16, "colpoymers" should read -- copolymers --.
Line 19, "coplymer" should read – copolymer --.

UNITED STATES PATENT AND TRADEMARK OFFICE
CERTIFICATE OF CORRECTION

PATENT NO. : 6,645,401 B2
DATED : November 11, 2003
INVENTOR(S) : Mark Giles et al.

It is certified that error appears in the above-identified patent and that said Letters Patent is hereby corrected as shown below:

Column 22,
Line 1, "OCO—, —OCO—O," should read -- —OCO—, —OCO—O—, --.
Line 6, "containing groups contain at least one" should read -- containing at least one --.

Column 22,
Line 17, "OCO—, —OCO—O," should read -- —OCO—, —OCO—O—, --.
Line 19, "are not directly" should read -- are not linked directly --.

Signed and Sealed this

Twenty-eighth Day of June, 2005

JON W. DUDAS
*Director of the United States Patent and Trademark Office*